(12) United States Patent
Boutzale et al.

(10) Patent No.: US 8,530,643 B2
(45) Date of Patent: Sep. 10, 2013

(54) CHLORINATION OF SUCROSE-6-ESTERS

(75) Inventors: Wayne N. Boutzale, Saraland, AL (US); David A. Dentel, Jurong Island (SG); Mohamad R. Jaber, Rancho Cucamonga, CA (US)

(73) Assignee: Tate & Lyle Technology Ltd., London (GB)

( * ) Notice: Subject to any disclaimer, the term of this patent is extended or adjusted under 35 U.S.C. 154(b) by 80 days.

(21) Appl. No.: 13/260,441

(22) PCT Filed: Mar. 24, 2010

(86) PCT No.: PCT/GB2010/000549
§ 371 (c)(1),
(2), (4) Date: Dec. 19, 2011

(87) PCT Pub. No.: WO2010/109189
PCT Pub. Date: Sep. 30, 2010

(65) Prior Publication Data
US 2012/0077972 A1    Mar. 29, 2012

Related U.S. Application Data

(60) Provisional application No. 61/164,075, filed on Mar. 27, 2009, provisional application No. 61/164,703, filed on Mar. 30, 2009.

(51) Int. Cl.
*C13K 5/00* (2006.01)
*C13K 7/00* (2006.01)
*C07H 1/00* (2006.01)
*C07H 3/00* (2006.01)

(52) U.S. Cl.
USPC ................................... 536/123.13

(58) Field of Classification Search
None
See application file for complete search history.

(56) References Cited

U.S. PATENT DOCUMENTS

| | | | |
|---|---|---|---|
| 4,980,463 | A | 12/1990 | Walkup et al. |
| 5,298,611 | A | 3/1994 | Navia et al. |
| 5,498,709 | A | 3/1996 | Navia et al. |
| 5,530,106 | A | 6/1996 | Navia et al. |
| 5,977,349 | A | 11/1999 | Catani et al. |
| 6,646,121 | B2 | 11/2003 | El Kabbani et al. |
| 6,809,198 | B2 | 10/2004 | El Kabbani et al. |
| 6,890,581 | B2 | 5/2005 | Vernon et al. |
| 6,943,248 | B2 | 9/2005 | Catani et al. |
| 6,998,480 | B2 | 2/2006 | Catani et al. |
| 7,049,435 | B2 | 5/2006 | Catani et al. |
| 2006/0188629 | A1 | 8/2006 | Liesen et al. |
| 2006/0205936 | A1 | 9/2006 | Jia et al. |
| 2006/0276639 | A1 | 12/2006 | Fry |
| 2007/0015916 | A1 | 1/2007 | El Kabbani et al. |
| 2007/0100139 | A1 | 5/2007 | Fry |
| 2007/0160732 | A1 | 7/2007 | Deshpande et al. |
| 2007/0227897 | A1 | 10/2007 | Li et al. |
| 2007/0270583 | A1 | 11/2007 | Ratnam et al. |

FOREIGN PATENT DOCUMENTS

| | | |
|---|---|---|
| EP | 0043649 | 1/1982 |
| EP | 0409549 | 1/1991 |
| EP | 0708110 | 4/1996 |
| WO | WO 2005/090374 | 9/2005 |
| WO | WO 2005/090376 | 9/2005 |

OTHER PUBLICATIONS

Hohmann, Birgit, International Search Report and Written Opinion dated Jul. 14, 2010.

*Primary Examiner* — Layla Bland
(74) *Attorney, Agent, or Firm* — RatnerPrestia

(57) ABSTRACT

A method for the chlorination of a sucrose-6-acylate to produce a 4,1',6'-trichloro-4,1',6'-trideoxy-galactosucrose-β-acylate wherein said method comprises: (i) reacting the sucrose-6-acylate with a chlorinating agent in a reaction vehicle comprising a tertiary amide in order to chlorinate the 4, V and 6' positions of the sucrose-6-acylate; and (ii) quenching the product stream of (i) to produce a 4,1',6'-trichloro-4, 1',6'-trideoxy-galactosucrose-6-acylate; wherein before said quenching, a portion of the tertiary amide is removed.

18 Claims, 1 Drawing Sheet

CHLORINATION OF SUCROSE-6-ESTERS

CROSS REFERENCE TO RELATED APPLICATIONS

This application is the national phase filing of international patent application No. PCT/GB2010/000549, filed 24 Mar. 2010, and claims priority of U.S. Appln. No. 61/164,075, filed 27 Mar. 2009, and U.S. Appln. No. 61/164,703, filed 30 Mar. 2009, the entireties of which applications are incorporated herein by reference.

FIELD OF THE INVENTION

The present invention relates to an improved method for the production of sucralose. In particular, the present invention relates to a method for the chlorination of a sucrose-6-acylate. Sucrose-6-acylate is an important intermediate in the production of sucralose.

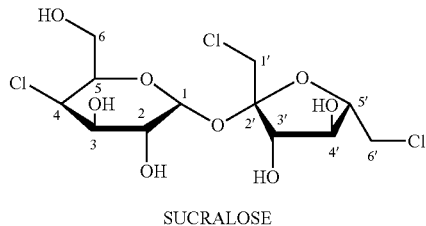

SUCRALOSE

BACKGROUND OF THE INVENTION

Methods for producing sucralose intermediates and sucralose from a feed stream comprising a sucrose-6-acylate in a reaction vehicle are known. For example, EP 0409549 discloses a process for the chlorination of a sucrose-6-acylate in a tertiary amide reaction vehicle to produce a sucrose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. The removal of the tertiary amide (which is usually dimethylformamide [DMF]) is carried out by steam stripping.

According to EP 0708110, it is preferred to perform the deacylation after the removal of the reaction vehicle, because otherwise, during the deacylation step, base-catalysed decomposition of the reaction vehicle, in this case a tertiary amide, occurs. This hinders the subsequent isolation of the sucralose, and also means that the tertiary amide cannot be efficiently recovered and recycled. Thus, the tertiary amide reaction vehicle is removed from an aqueous solution of sucralose-6-acylate, and deacylation of the sucralose-6-acylate is carried out thereafter.

A process for the recovery of the tertiary amide prior to deacylation is disclosed in U.S. Pat. No. 5,530,106. This process involves steam stripping.

The steam stripping according to these prior art methods is very energy intensive.

The disadvantages of the known steam stripping process for removal of the reaction vehicle are discussed in WO 2005/090376 and WO 2005/090374. These references propose removal of all liquids after quench of the chlorination reaction to provide a solid residue, and to then obtain sucralose from the solid residue. According to this prior art, the removal of the liquids preferably takes place using an agitated thin film dryer.

SUMMARY OF THE INVENTION

With the above in mind, the present inventors have devised an improved process for the production of sucralose.

The present invention seeks to provide a chlorination process in the presence of a tertiary amide such as DMF which is more energy efficient whilst minimising any potential negative impact upon yield.

The present invention now provides a method for the chlorination of a sucrose-6-acylate to produce a 4,1',6'-trichloro-4,1',6'-trideoxy-galactosucrose-6-acylate wherein said method comprises:
(i) reacting the sucrose-6-acylate with a chlorinating agent in a reaction vehicle comprising a tertiary amide in order to chlorinate the 4, 1' and 6' positions of the sucrose-6-acylate; and
(ii) quenching the product stream of (i) to produce a 4,1',6'-trichloro-4,1',6'-trideoxy-galactosucrose-6-acylate; wherein before said quenching, a portion of the tertiary amide is removed.

A 4,1',6'-trichloro-4,1',6'-trideoxy-galactosucrose-6-acylate can also be referred to as a sucralose-6-acylate, so that 4,1',6'-trichloro-4,1',6'-trideoxy-galactosucrose-6-acetate can also be referred to as sucralose-6-acetate. Both terminologies are used herein.

DETAILED DESCRIPTION OF THE INVENTION

Figure 1:
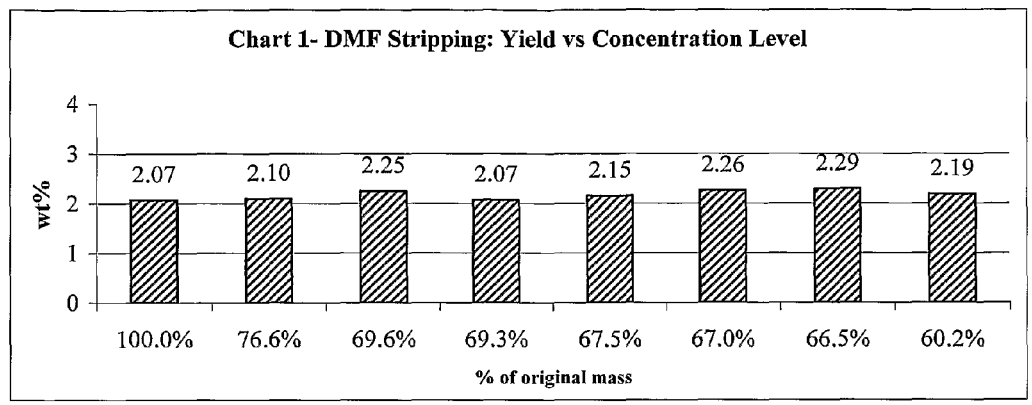
FIG. 1 is a bar chart showing the effect of different degrees of DMF removal on sucralose-6-acetate yield.

It has now been found that a large portion of the chlorination reaction vehicle (comprising a tertiary amide such as DMF) may be removed directly from the reaction mixture by distillation before quenching. The resulting distillate is typically made up primarily of the reaction vehicle comprising the tertiary amide along with some acid (typically HCl, in particular when phosgene or Arnold's reagent is used as the chlorinating agent). Since the distillate is primarily the reaction vehicle comprising the tertiary amide, it becomes possible to purify the reaction vehicle comprising the tertiary amide in a much more energy efficient way (little to no water separation, so that steam stripping is unnecessary). If the concentrated residue is eventually quenched with caustic solution as usual, then, surprisingly, there is little negative impact to the yield of the chlorination product and hence also the sucralose. A large percentage of the reaction vehicle comprising the tertiary amide can be removed prior to adding water in the quench step, and, if distillation is employed, the energy required in the downstream distillation processes to remove the remainder of the reaction vehicle comprising the tertiary amide is dramatically reduced. Furthermore, the stripped tertiary amide requires only minor processing, for example to remove acid, before recycling.

The process of the present invention also has the advantage of decreasing exposure of the tertiary amide to basic conditions, thus reducing losses of the tertiary amide due to hydrolysis in the chlorination quench, and also in the subsequent deacylation step, if deacylation is carried out before removal of the remaining tertiary amide. In addition, since the material is dry (i.e. essentially no water content) at the time of the removal of the tertiary amide according to the method of the present invention, less energy is required to remove the tertiary amide from the unquenched chlorination mixture. The stripped tertiary amide reaction vehicle is dry and of an acceptable quality. In some embodiments, the stripped tertiary amide can be recycled for further use with no further treatment. In other embodiments, the stripped tertiary amide only requires minor processing, for example to remove acid, before recycling.

Preferably, the tertiary amide is removed by distillation. Preferably also, this distillation is conducted under reduced pressure, typically from 1 torr to 200 torr (0.13 to 26.7 kPa), more preferably from 10 torr to 100 torr (1.3 to 13.3 kPa), most preferably from 35 torr to 65 torr (4.7 to 8.7 kPa). The tertiary amide so distilled may be recycled to be used as solvent in a step in the synthesis of sucralose from sucrose. For example, it may be recycled to be used as solvent in the chlorination step of the overall reaction sequence.

The removal of the tertiary amide is typically carried out at an internal temperature of from 40° C. to 150° C., more typically from 50° C. to 90° C. The removal of the tertiary amide can be carried out in a batch or continuous manner. In a batch manner, the removal of the tertiary amide is typically carried out over a time period of from 1 hour to 24 hours. The temperature, pressure, and time required are interrelated, and optimum conditions can be determined by the person skilled in the art according to the operating requirements of the process and the equipment used. In general, the removal of the tertiary amide is carried out as rapidly as possible. If longer time periods are used for the removal of the tertiary amide, then it is preferred to use lower temperatures, in order to minimise carbohydrate degradation.

The removed tertiary amide can be recycled for further use in the method, or other step in the synthesis of sucralose from sucrose. If required, the removed tertiary amide can be treated with a base, and filtered if necessary, to remove hydrogen chloride before being recycled. Suitable bases are hydroxides and carbonates of alkali and alkali earth metals, such as sodium hydroxide, potassium hydroxide, calcium hydroxide, sodium carbonate, potassium carbonate, and calcium carbonate. Ammonia can also be used. The base can be an anhydrous base or an aqueous solution or suspension of the base.

The amount of tertiary amide removed is typically from 5% to 80% by weight of the product stream of (i), more preferably from 10% to 50% by weight of the product stream of (i), still more preferably from 20% to 50% by weight of the product stream of (i), and most preferably from 30% to 45% by weight of the product stream of (i). Preferably also, the amount of tertiary amide removed is such that the resulting concentrated mixture contains from 5% to 90% by weight of the tertiary amide, preferably from 10% to 85% by weight of the tertiary amide, more preferably from 40% to 80% by weight of the tertiary amide, still more preferably from 50% to 70% by weight of the tertiary amide, and most preferably from 50% to 60% by weight of the tertiary amide. In particular, if no co-solvent (discussed further below) is employed, the amount of tertiary amide removed is preferably such that the resulting concentrated mixture contains from 25% to 85% by weight of the tertiary amide.

It is preferred that the residue stays warm (typically from 40° C. to 150° C., more typically from 40° C. to 125° C. and most typically from 40° C. to 60° C.) after it is concentrated, because if the concentrated residue is allowed to cool, it can become too viscous to handle easily.

Following chlorination and removal of a portion of the tertiary amide reaction vehicle according the present invention, the process stream is quenched, for example with a base, to provide a sucralose-6-acylate and the acid salt of the base.

A number of different bases may be used in the quenching. Preferred bases for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most preferred base for quenching is sodium hydroxide, due to its ready availability and low cost. Other bases known to the skilled person may also be used for quenching. The quench is preferably performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50 wt %, preferably from 25 to 45 wt %, more preferably about 35 wt %. If the solution of the base is dilute, precipitation of salts is not envisaged, and in that case suitable concentrations are from 5 to 15 wt %, preferably from 8 to 13 wt %, more preferably from 10 to 11 wt %.

During the quenching, the pH of the process stream should preferably be controlled, since it is generally preferred that deacylation should be minimised while quenching takes place. This pH control is readily achievable by controlling the addition rate of the aqueous solution of the base while monitoring the pH within the process stream. Any method of pH-controlled addition known to the skilled person may be used.

Suitably, the pH of the stream is maintained in the range of from about 7.5 to about 10.5 during the quenching, preferably from about 8.5 to about 10.5, more preferably from about 9.5 to about 10, more preferably from about 9.5 to about 9.75. Optionally, the pH may be maintained at a lower level, for example about 4.5, during the addition, and then raised to the preferred pH when all of the base has been added. If deacylation is to be carried out as a separate step, though, a pH of more than about 10 should generally be avoided during quenching, since deacylation may then occur. In order to avoid local extremes of pH, the reaction mixture should be adequately mixed throughout the quenching procedure.

The temperature of the stream during quenching may suitably be maintained in the range of from above 0° C. to about 80° C., for example, in the range of from 10° C. to 60° C., with a range of from about 12° C. to about 35° C. being preferred.

The quench is preferably conducted by the "dual stream quench" method, which is described in U.S. Pat. Nos. 5,530,106 and 5,498,709.

In the dual stream process, the quenching conditions are attained by slow addition of the aqueous base with simultaneous slow addition of feed material into a reaction vessel. The reaction vessel can contain an initial charge of an aqueous solution of the tertiary amide such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction. Preferably, the pH should not be permitted to rise above about 10.5 during the course of the quenching reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode. Preferably, the pH should not be permitted to rise above about 10.5 during the course of the quenching reaction.

Following quenching, the reaction mixture may be neutralised by the addition of aqueous acid, for example aqueous hydrochloric acid. The sucralose-6-acylate can then be isolated by conventional means, if desired, or deacylation can be carried out without isolation of the sucralose-6-acylate.

As used herein, the term "reaction vehicle" means the diluent or solvent in which the chlorination reaction is performed. The term is meant to indicate that the vehicle may not fully dissolve all the components of the reaction and product mixture. Depending on the chlorinating agent employed, a number of types of reaction vehicles may be used, and any reaction vehicle can be used that is stable under the chlorination conditions and that dissolves the starting materials, reagents, and products at least to some extent. The reaction vehicle according to the present invention comprises a tertiary amide. The tertiary amide reaction vehicle is preferably DMF. The ratio by weight of the tertiary amide reaction vehicle, for example DMF, to total carbohydrate during the chlorination reaction may be about 5:1 to about 12:1.

The reaction vehicle may additionally comprise one or more co-solvents, in addition to the tertiary amide. Suitable co-solvents are selected from the group consisting of 1,2-dichloroethane, 1,2-diethoxyethane, toluene, o-xylene, m-xylene, p-xylene, chloroform, dichloromethane, and mixtures thereof.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

The chlorination reaction in the method of the present invention can be carried out by a number of methods, such as those disclosed in EP 0043649, EP 0409549, US 2006/0205936, and US 2007/0100139.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene)dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis(trichloromethyl)carbonate). Other suitable chlorinating agents known to the skilled person may also be used. Preferably, the chlorinating agent is phosgene or Arnold's reagent.

The chlorinating agent is preferably added in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating is any amount above three molar equivalents per mole. In a preferred embodiment, the chlorinating agent is added in an amount of at least seven molar equivalents per mole of the sucrose-6-acylate. Typically, the molar ratio of the chlorinating agent to the sucralose-6-acylate is about 7:1 to about 11:1.

A number of reaction conditions can be used to achieve the chlorination according to the present invention. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, U.S. 2007/0100139, the disclosure of which is incorporated herein by reference, discloses a process in which the reaction mixture is heated between 75° C. to 100° C. to effect chlorination.

In general, the reaction temperature for the chlorination reaction according to the present invention is typically from 85° C. to 130° C.

The reaction time for the chlorination according to the present invention depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products.

The present invention also extends to a method of producing sucralose by deacylating at least a portion of the 4,1',6'-trichloro-4,1',6'-trideoxy-galactosucrose-6-acylate to form the sucralose. The deacylation can be performed before or after the removal of the remaining tertiary amide reaction vehicle, but is preferably performed before the removal of the remaining tertiary amide reaction vehicle.

The deacylation can be carried out, for example, by the method disclosed in U.S. Pat. No. 6,890,581, incorporated herein in its entirely by reference. Other methods for deacylating sucralose-6-acylates, and for isolating and/or purifying sucralose, are disclosed in U.S. Pat. No. 5,977,349, U.S. Pat. No. 6,943,248, U.S. Pat. No. 6,998,480, U.S. Pat. No. 7,049,435, U.S. Pat. No. 6,809,198, U.S. Pat. No. 6,646,121, U.S. Pat. No. 5,298,611, U.S. Pat. No. 5,498,709, US2006/0188629, US2006/0276639, US2007/0015916, US2007/0160732, and US2007/0270583, the disclosures of which are all incorporated herein by reference.

The deacylation can be carried out by treatment with a base. Any suitable base may be used, and suitable bases are those already mentioned as the base for quenching. For convenience, it is preferred to use the same base for deacylation and quenching. It is particularly preferred to use sodium hydroxide as the base in both cases.

In order to effect deacylation, it is necessary to raise the pH of the stream, typically to a level above that at which the quenching was carried out. In order to minimise decomposition of the tertiary amide reaction vehicle (if the deacylation is performed before the removal of remaining tertiary amide reaction vehicle), the deacylation is preferably carried out under carefully controlled conditions. Therefore, the deacylation is preferably performed at a pH of from 10 to 13.5, more preferably from 10 to 12, and most preferably from 10.5 to 11.2, at a temperature of from 60 to 0° C., more preferably from 40 to 0° C., and most preferably from 35° C. to 25° C., the higher pH being used with the lower temperature and vice versa.

If the deacylation is carried out after the removal of remaining tertiary amide reaction vehicle, then the deacylation conditions are less critical, although the above described conditions can still be used. In general, the deacylation may be carried out at a pH of from 8 to 14 and a temperature of from 0 to 60° C., preferably at a pH of from 10 to 12 and a temperature of from 0 to 40° C.

The deacylation reaction can be conveniently monitored by HPLC. For optimum yields, it is important to monitor the progress of the deacylation reaction, and neutralise the reaction mixture when the reaction is complete. The pH of the reaction mixture should be adjusted to from 6 to 8.5, preferably approximately 7.5. The reaction mixture can conveniently be neutralised using aqueous hydrochloric acid, or using citric acid or acetic acid. Alternatively, the reaction mixture can be neutralised with gaseous carbon dioxide.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in the preferred embodiment described above, it is also possible for quenching and deacylation to be carried out together. In this embodiment, the aqueous solution of a base is added to the chlorination product stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

The removal of remaining reaction vehicle can be carried out by means known in the art, such as distillation, distillation under reduced pressure, steam distillation, steam stripping, or by use of an agitated thin film drier or spray drier. It is preferred that the removal of the reaction vehicle is carried out by steam stripping. Such steam stripping can be carried out as described in EP 0708110. Typically, at least 90% of the reaction vehicle present in the mixture at the end of deacylation (if the removal of the reaction vehicle is carried out after deacylation), or after the quench of the chlorination reaction, (if the removal of the reaction vehicle is carried out before the deacylation) is removed during this step. More typically, at least 99% is removed.

The present invention will now be explained in more detail by reference to the following Examples, and with reference to the accompanying drawings, in which:

FIG. 1 is a bar chart showing the effect of different degrees of DMF removal on sucralose-6-acetate yield. Percent weights were determined after subsequent dilution to the same mass so that percent weights are directly proportional to respective yields.

Figure 2:
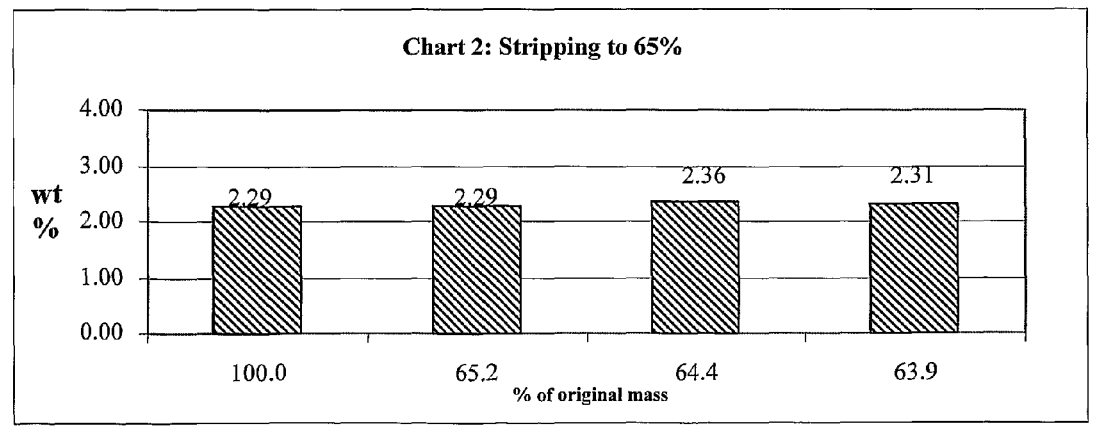
FIG. 2 is a bar chart showing the effect on sucralose-6-acetate yield for three repeat runs at DMF removal to 65% against a control with no DMF removal.

FIG. 2 is a bar chart showing the effect on sucralose-6-acetate yield for three repeat runs at DMF removal to 65% against a control with no DMF removal. Percent weights were determined after subsequent dilution to the same mass so that percent weights are directly proportional to respective yields.

EXAMPLES

The yields when reducing the unquenched chlorination mass to different levels by stripping DMF are compared. It is found that there is no significant negative impact on yield. Thus, an efficient and less energy demanding process for DMF removal from a dry mixture prior to quench and mixing with caustic/water has been shown to be practical.

Method

The feed stream comes from the acetylation of sucrose. Such a feed stream can be produced, for example, by the methods disclosed in U.S. Pat. No. 5,470,969. A typical composition of the feed stream is as follows:

| Description | % of total, w/w |
|---|---|
| Sucrose-6-acetate | 29.4 |
| Other carbohydrates | 10.4 |
| DMF | 52.7 |
| Others | 7.5 |

The chlorination is conducted as follows:
1. 25 g of Arnold's reagent is charged to a 250 mL round bottom flask equipped with a stirrer bar.
2. Approximately 50 g of DMF is added to the flask.
3. The slurry is cooled to 0-5° C.
4. 20 grams of carbohydrate feed is added dropwise at temperature <20° C.
5. After addition is complete, the mixture is stirred at room temperature for 3-4 hours followed by heating at 100° C. for 11 hours.
6. The mixture is cooled and quenched as described below.

Trials of DMF removal before quench are conducted as follows:
A. Unquenched chlorination material (100 g) is transferred to a 250 mL round-bottomed flask. The flask is attached to a rotary evaporator equipped with 100 mL graduated cylinder with a round joint for catching flashed solvent. The flask is immersed in a water bath set for ~80° C., and the solvent is flashed to different levels (0-45% removed of the original mass) under vacuum. The amount of solvent removed is estimated by reading the volume in the graduated cylinder and eventually confirmed by weighing the residue in the round-bottomed flask. The residue is then taken into the quench step prior to yield analysis.
B. The chlorination residue is quenched using 11% NaOH at pH 9.75 and 20° C. using the "dual stream" quench method. After the quench, all chlorination quench mixtures are diluted to the same mass with water prior to analysis so that the weight percent of carbohydrate can be used as a direct measure of reaction yield.
C. Assessment of weight % of sucralose-6-acetate is made by usual analytical techniques such as chromatography.

Results

FIG. 1 of the accompanying drawings shows that there is no adverse effect on yield of trichlorinated sucralose-6-acetate as the dry chlorination material is concentrated by DMF removal to different levels followed by quenching the residue by the normal protocol. All quenched masses are diluted with water to the same level for analytical comparison. The concentration, and thus yield, stays almost constant between 2.07 and 2.29 wt % as the material mass is reduced to 60.2% of the original starting mass. The result given in FIG. 1 for the 100% of original mass run is an average of triplicate runs that does not involve any DMF removal (hence 100% of original mass).

This average is used as a control for the process performance. All other batches are single runs since it would be hard to replicate the DMF removal to exactly the same level more than once on the rotary evaporator.

To study the scope of this work a little further, unquenched chlorinated mixture is reduced to ~65% of the original mass by removing DMF from the mixture. The residue is quenched as before (see FIG. 2). Yields for sucralose-6-acetate range between 2.29 and 2.36 wt % against 2.29 wt % for the control, which is not stripped.

In summary, it is possible to remove DMF from a dry chlorination mixture prior to quench with caustic and deacetylation. The chlorination product yield is not compromised. In the present work, concentration of the unquenched chlorination mixture to approximately 60% by weight of the mixture original mass is performed with little negative impact on the chlorination yield.

After removal of the solvent, it is found to be beneficial to keep the residue warm during transfer to the quench vessel to prevent it from thickening.

The recovered DMF is analyzed for impurities present, and it is found to be consistently ≧95% by GC. The major impurity component is determined to be HCl present at ~2-4%. If the HCl presence at that level can be tolerated, the recovered DMF can be used subsequently without any further purification. However, it will often be desirable to remove HCl. Accordingly, the recovered DMF is treated with aqueous bases such as 20% NaOH and 23% $Na_2CO_3$. Stoichiometric amounts of bases are used and solids generated are filtered. Alternatively, the HCl contaminated DMF is treated with a variety of bases under dry conditions to keep the water level as low as possible. The bases that are used cover soda ash ($Na_2CO_3$), lime ($Ca(OH)_2$), dry caustic (NaOH) and ammonia ($NH_3$). The operating temperatures range from room temperature to 90° C. Suspensions obtained are filtered. Performance of the bases vary, with soda ash and ammonia giving the best results.

Example 1

Unquenched chlorination material (100 g) is transferred to a 250 mL round-bottomed flask. The flask is attached to a rotary evaporator equipped with 100 mL graduated cylinder with a round joint for catching flashed solvent. The flask is immersed in a water bath set for ~80° C., and the solvent is flashed to different levels (0-45% removed of the original mass) under vacuum. The amount of solvent removed is estimated by reading the volume in the graduated cylinder and eventually confirmed by weighing the residue in the round-bottomed flask. The residue is then taken into the quench step prior to yield analysis.

The chlorination residue quench is conducted by the "dual stream" quench method at pH 9.75 and 20° C. using 11% NaOH. After the quench, all chlorination quench mixtures are diluted to the same mass with water prior to analysis to give consistent analytical readings. The results are shown in FIG. 1.

Example 2

Unquenched chlorination material (100 g) is transferred to a 250 mL round-bottomed flask. The flask is attached to a rotary evaporator equipped with 100 mL graduated cylinder with a round joint for catching flashed solvent. The flask is immersed in a water bath set for ~80° C., and the solvent is flashed to remove ~35% of the original mass under vacuum. The amount of solvent removed is estimated by reading the volume in the graduated cylinder and eventually confirmed by weighing the residue in the round-bottomed flask. The residue is then taken into the quench step prior to yield analysis.

The chlorination residue quench is conducted by the "dual stream" quench method at pH 9.75 and 20° C. using 11% NaOH. After the quench, all chlorination quench mixtures are diluted to the same mass with water prior to analysis to give consistent analytical readings. The results are shown in FIG. 2.

Example 3

To 199.5 g of DMF contaminated with HCl (4.35 wt %) is added 15.8 g of $Na_2CO_3$ at 60° C. After addition is completed, heating the mixture at 60° C. is maintained for 6 hours. An aliquot taken from the reaction mixture is filtered and then analyzed. Analysis indicates a drop of the HCl level to 285 ppm.

The invention claimed is:
1. A method for the chlorination of a sucrose-6-acylate to produce a 4,1',6'-trichloro-4,1',6'-trideoxy-galactosucrose-6-acylate wherein said method comprises:
   reacting the sucrose-6-acylate with a chlorinating agent in a reaction vehicle comprising a tertiary amide in order to chlorinate the 4, 1' and 6' positions of the sucrose-6-acylate; and
   (ii) quenching the product stream of (i) to produce a 4,1',6'-trichloro-4,1',6'-trideoxy-galactosucrose-6-acylate;
   wherein before said quenching, a portion of the tertiary amide is removed.
2. The method according to claim 1, wherein the tertiary amide is removed by distillation.
3. The method according to claim 2, wherein the distillation is conducted under reduced pressure.
4. The method according to claim 1, wherein the amount of tertiary amide removed is from 5 to 80% of the weight of the product stream of (i).
5. The method according to claim 1, wherein the amount of tertiary amide removed is such that the resulting mixture contains from 5% to 90% by weight of the tertiary amide.
6. The method according to claim 1, wherein the temperature is from 40 to 150° C. during the removal of the tertiary amide and is maintained within this range until the quenching.
7. The method according to claim 1, wherein the tertiary amide is DMF.
8. The method according to claim 1, wherein the chlorinating agent is phosgene or Arnold's reagent.
9. The method according to claim 1, wherein the sucrose-6-acylate is sucrose-6-acetate.
10. The method according to claim 1, wherein the sucrose-6-acylate is sucrose-6-benzoate.
11. The method according to claim 1, wherein the removed tertiary amide is recycled for further use in the method.
12. The method according to claim 1, wherein the removed tertiary amide is recycled for use in a step in the synthesis of sucralose from sucrose.
13. The method according to claim 11, wherein the removed tertiary amide is treated with a base to remove hydrogen chloride before being recycled.
14. The method according to claim 13, wherein the removed tertiary amide is filtered following treatment with the base.

15. The method according to claim 1, which further comprises the step of converting at least a portion of said 4,1',6'-trichloro-4,1',6'-trideoxy-galactosucrose-6-acylate to sucralose.

16. The method according to claim 15, which further comprises the step of isolating and purifying the sucralose.

17. The method according to claim 12, wherein the removed tertiary amide is treated with a base to remove hydrogen chloride before being recycled.

18. The method according to claim 17, wherein the removed tertiary amide is filtered following treatment with the base.

* * * * *

UNITED STATES PATENT AND TRADEMARK OFFICE
CERTIFICATE OF CORRECTION

PATENT NO. : 8,530,643 B2
APPLICATION NO. : 13/260441
DATED : September 10, 2013
INVENTOR(S) : Wayne N. Boutzale, David A. Dentel and Mohamad R. Jaber Page 1 of 1

It is certified that error appears in the above-identified patent and that said Letters Patent is hereby corrected as shown below:

In the Claims:

At Column 10, line 26, before the word "reacting" please insert -- (i) --

Signed and Sealed this
Twenty-ninth Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,530,643 B2
APPLICATION NO. : 13/260441
DATED : September 10, 2013
INVENTOR(S) : Boutzale et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this

Fifteenth Day of September, 2015

Michelle K. Lee
*Director of the United States Patent and Trademark Office*